United States Patent [19]
Eibling

[11] Patent Number: 5,284,141
[45] Date of Patent: Feb. 8, 1994

[54] ELECTRODE EMPLACEMENT APPARATUS FOR AMNIOTOMY AND FETAL MONITORING AND METHOD OF USE

[76] Inventor: David L. Eibling, 1617 N. California St., Ste. 2-A, Stockton, Calif. 95204

[21] Appl. No.: 922,396

[22] Filed: Jul. 31, 1992

[51] Int. Cl.⁵ .................... A61B 5/0448; A61B 17/42
[52] U.S. Cl. ..................................... 128/642; 606/125
[58] Field of Search ........................ 128/642; 606/125

[56] References Cited

U.S. PATENT DOCUMENTS 3,472,234 10/1969 Tachick .
3,533,411 10/1970 McKnight et al. ................. 606/125
3,580,242 5/1971 La Croix .
3,750,650 8/1973 Ruttgers .
3,827,428 8/1974 Hon et al. .

*Primary Examiner*—Lee S. Cohen
*Attorney, Agent, or Firm*—Douglas E. White

[57] ABSTRACT

The present invention comprises a barb or hook attached on a side of the forward end of the outer guide tube of an otherwise standard electrode introducer sleeve. The hook enables the physician to perforate the membrane within the same single vaginal exam wherein the electrode is attached. A costly, time-consuming, and uncomfortable two-stage, two-tool medical procedure is reduced to one stage and one tool.

16 Claims, 3 Drawing Sheets

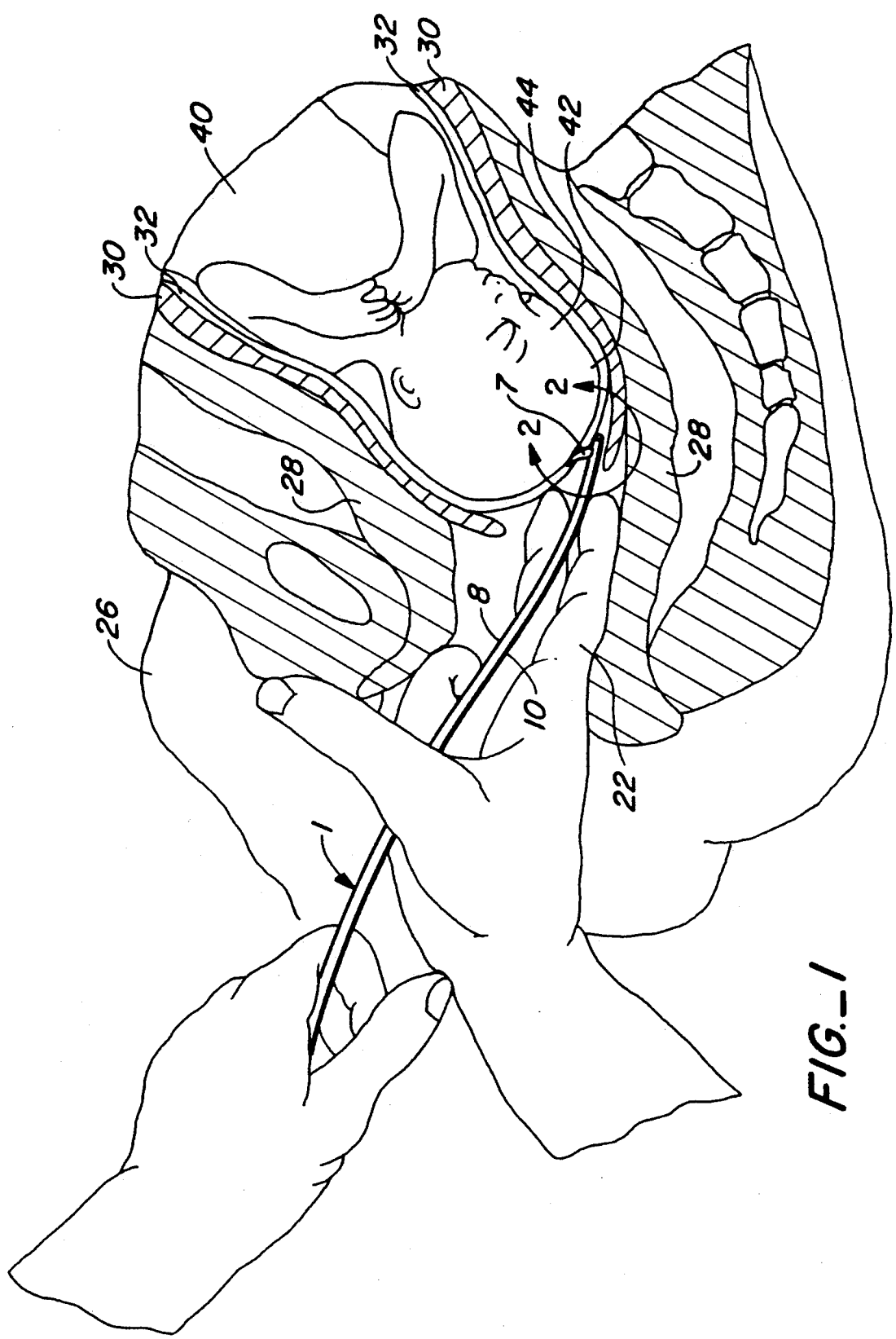
FIG._1

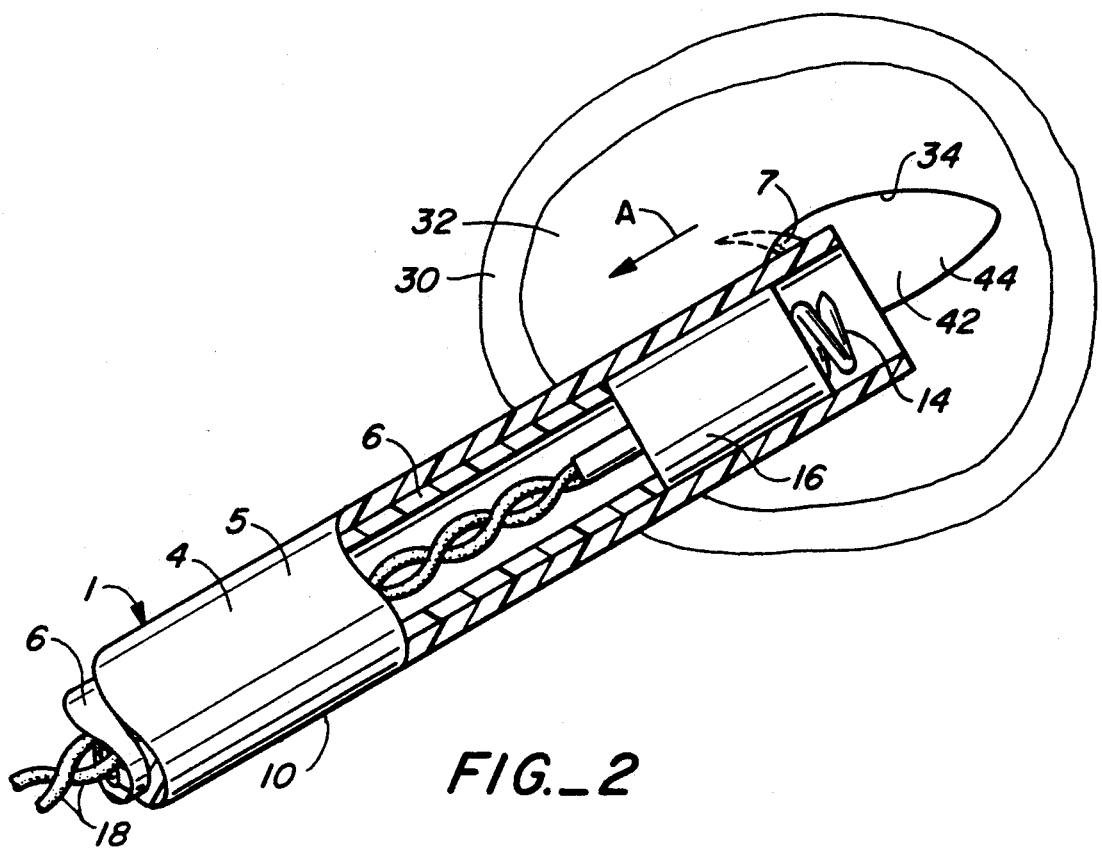
FIG._2
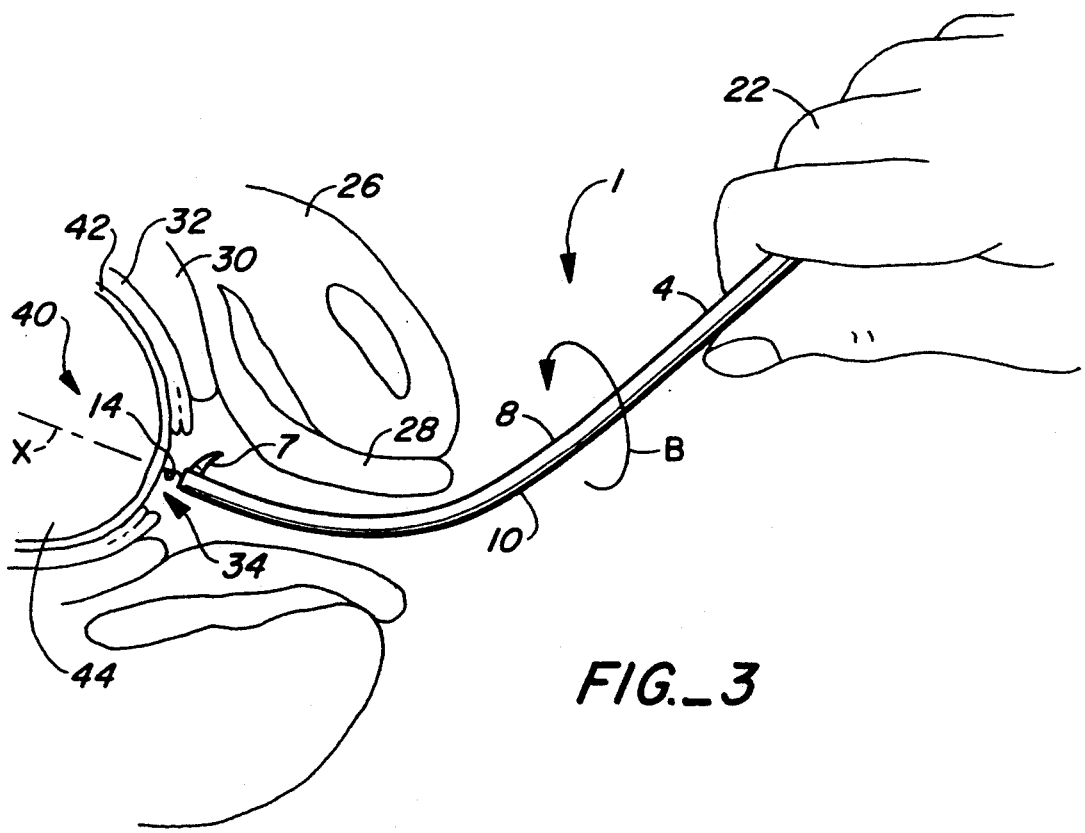
FIG._3

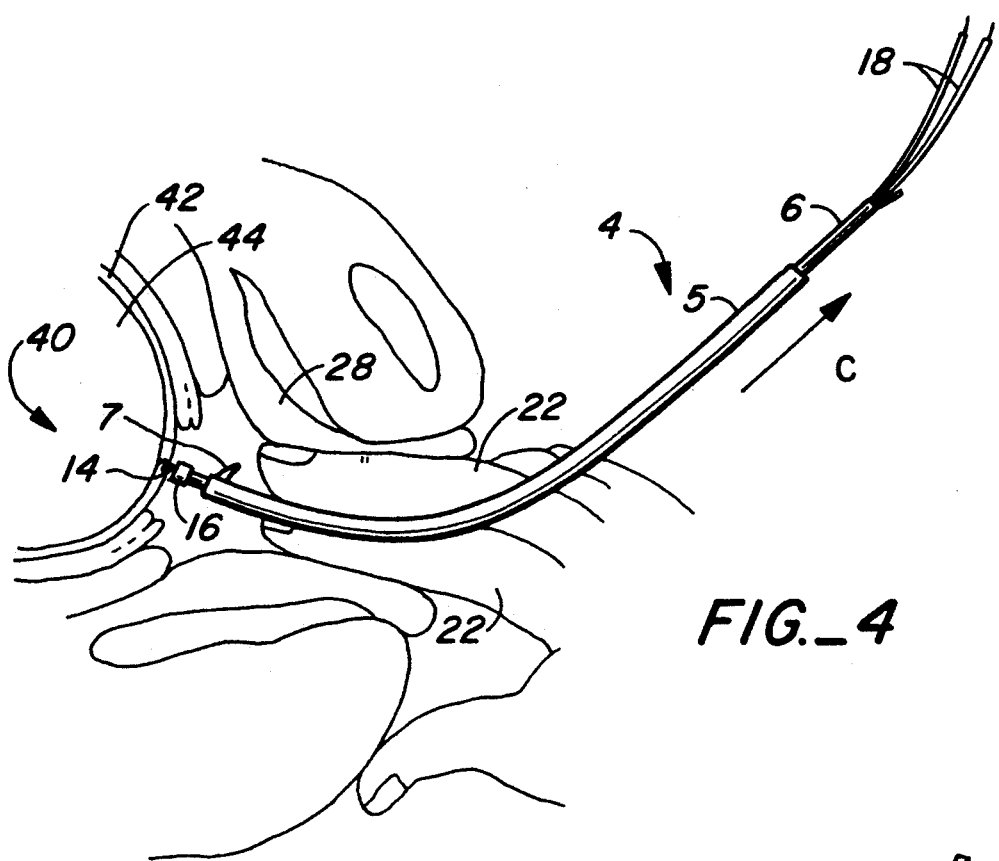
FIG._4
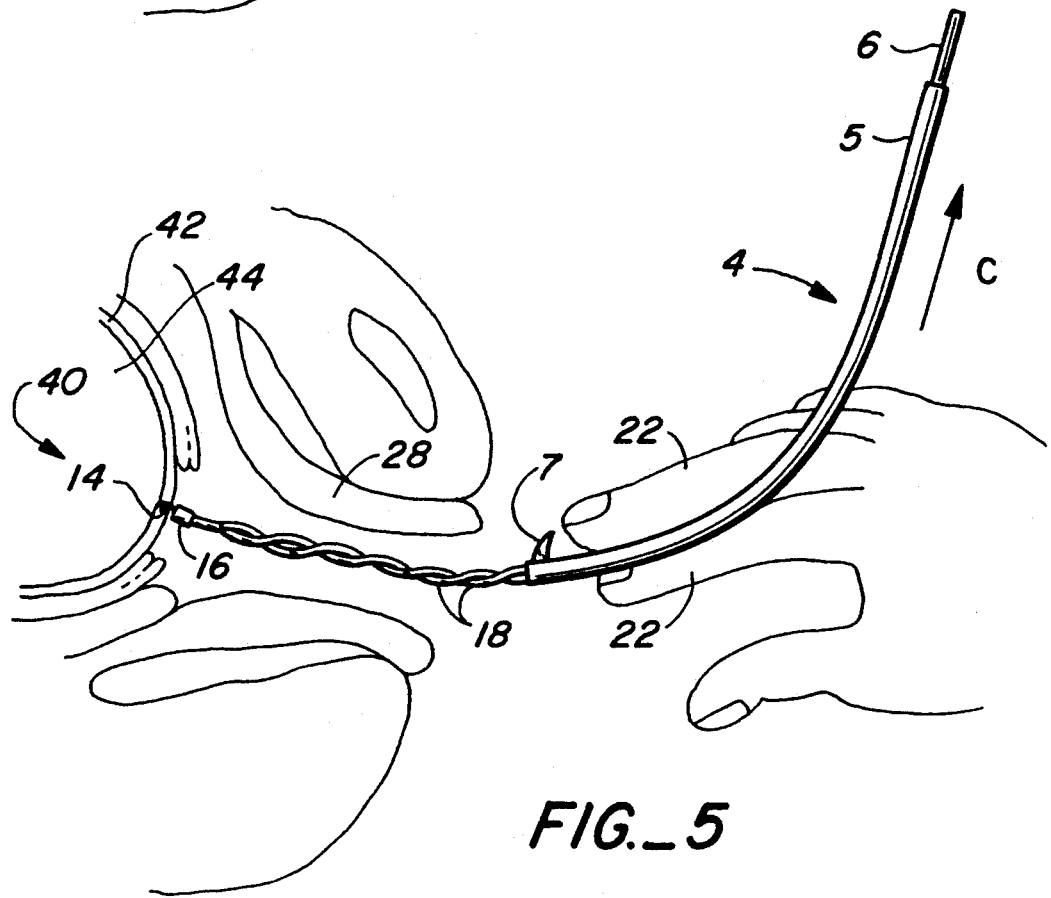
FIG._5

ELECTRODE EMPLACEMENT APPARATUS FOR AMNIOTOMY AND FETAL MONITORING AND METHOD OF USE

FIELD OF THE INVENTION

This invention relates to fetal scalp electrodes, more particularly to a heart rate monitoring electrode whose introducer sleeve apparatus incorporates a membrane-perforating hook.

BACKGROUND OF THE INVENTION

Presently, to prepare for intrapartum fetal heart rate monitoring wherein the fetal amniotic membranes have not ruptured naturally, one must first perform an amniotomy, i.e. an artificially forced rupturing of the membranes. This must be done in order to provide the fetal electrode with clear, clean and direct access to the presenting part of the fetus.

It is therefore known to introduce into the birth canal, as a first and separate procedure, a barbed amniotic membrane perforator, such as the elongate plastic perforator sold under the trade name AMNIHOOK by Hollister Inc. of Libertyville, Ill. Finger cot amniohooks and other barbed perforator devices are also available. The perforator is dragged sideways across the fetal amniotic membranes so as to hook and rupture them. The perforator is then removed from the birth canal.

Next, it is also known, as a second and separate procedure, to introduce a spiral electrode into the birth canal and to screw it into the now-exposed fetal scalp, or into the epidermis of another fetal presenting part. This is accomplished by means of a curved introducer sleeve apparatus having a smooth-surfaced (non-barbed) external guide tube. The introducer sleeve is then removed from the birth canal. This leaves the electrode in place, which electrode is connected to an electrocardiogram-type recording device, or other sensing equipment, in order to allow intrapartum fetal heart rate monitoring.

Prior developments in this field may be generally illustrated by reference to the following information disclosure statement:

| Pat. No. | Patentee | Issued |
| --- | --- | --- |
| 3,827,428 | Hon et al. | Aug. 06, 1974 |
| 3,580,242 | La Croix | May 25, 1971 |
| 3,750,650 | Ruttgers | Aug. 07, 1973 |
| 3.472,234 | Tachick | Oct. 14, 1969 |

Published articles which are of interest include: Hon et al., "Electronic Evaluation of Fetal Heart Rate", Vol. 40 *Obstetrics and Gynecology*, pp. 362 et seq. (September 1972); Paul et al., "Clinical Fetal Monitoring", Vol. 41 *Obstetrics and Gynecology*, pp. 777 et seq. (May 1973); and Fukushima et al., "An Improved Spiral Electrode Applicator System for Fetal Heart Rate Monitoring", Vol. 77 *Obstetrics and Gynecology*, pp. 475 et seq. (March 1991).

The first crude fetal scalp electrode was introduced about 1971 by George LaCroix. In 1973, Helge Ruttgers developed a double spiral electrode for fetal heart rate monitoring. Neither of these devices received widespread acceptance.

In 1974, Edward Hon developed the bipolar electrode and introducer sleeve which is described in U.S. Pat. No. 3,827,428 and which is currently the device most commonly used in this and other countries for internal fetal heart rate monitoring.

Currently, there are four million deliveries annually in the United States. About eighty per cent of these utilize fetal heart rate monitoring. Up to eighty or ninety per cent of the latter subgroup require amniotomies.

As noted above, where the membranes have not ruptured spontaneously, the Hon electrode cannot be applied without first performing, in a separate procedure, an amniotomy with another device. This is unfortunate because each birthing facility must order, inventory, stock, and quickly and reliably find, if and when needed, a membrane perforator for most deliveries where an electrode will be applied. Of course, the scalp electrode, including introducer sleeve apparatus, must be separately stocked and located. The need to stock two separate items effectively doubles the risk that a procedure will not be performed in a timely manner due to one of the items being misplaced, out of stock, accidentally rendered septic, or the like.

One of the most uncomfortable events for a patient in labor is the vaginal exam, which procedure involves penetration by instruments and/or the fingers of the attending practitioner. As noted, present practice involves two separate intrusions in order to attach the scalp electrode. The practitioner must do a vaginal exam to rupture the membranes, withdraw his hands from the vagina, change instruments and then re-enter the vagina to apply the electrode to the fetus.

Thus, patients would appreciate the decrease in discomfort that would result from combining these two procedures into one. Physicians would appreciate the savings in time and the increase in focus and control gained by such simplification. Not only would patients also appreciate the savings in time, but in cases where time is of the essence, such savings and simplification could provide significant benefits in health and safety, and result in fewer errors. Both the birthing facility and its patients would appreciate the savings in material and expense that would result from the elimination of one type of apparatus.

SUMMARY OF THE INVENTION

The present invention comprises a barb or hook attached on the side of the forward end of the outer guide tube of an otherwise standard electrode introducer sleeve. The hook enables the physician to perforate the membranes within the same single vaginal exam wherein the electrode is attached. While, once revealed, the new apparatus is relatively simple, its unanticipated beneficial effect is significant. A costly, time-consuming, and uncomfortable two-stage, two-tool medical procedure is reduced to one stage and one tool, as discussed above. Thus, the combination results in a synergistic result; i.e., rather than merely being a combination of two tools into one tool which is used in the same manner as were the two, a new tool renders possible a safe and simple procedure which was not heretofore attainable.

FEATURES AND ADVANTAGES

An object of this invention is to simplify amniotomy and fetal monitoring electrode attachment procedures by combining the two procedures through the use of a single apparatus.

An advantage of the apparatus of this invention is that it eliminates the need for a separate amnio-hook or finger cot. Facilities will be required to order, inventory and keep sterile only a single instrument, rather than the two or three presently required.

The valuable time of the nurse and obstetrician will be saved by eliminating the need to locate two instruments under hurried circumstances. In some cases, the time saved may represent the difference between life and death.

Another advantage is that patients will experience the benefit of reduced discomfort due to the elimination of one separate vaginal examination involving penetration. Achieving lowered anxiety and increased mental well-being during the inherently complex and dangerous process of labor conceivably may reduce morbidity rates in and of itself.

A further advantage is that the fetus also will have to endure less vaginal exams. This will reduce morbidity by lowering fetal infection rates (as well as maternal-)—an extra route for introducing infection being inherent in the two-tool procedure. Mental stress on the fetus should also be reduced, from which only beneficial results can be foreseen. Furthermore, expectant mothers can be assumed strongly to desire that the fetus be unnaturally disturbed as seldom as possible.

A further advantage is that the apparatus can be mass produced at relatively low cost with currently available techniques, requiring only minimal modification.

Yet another feature or advantage is that the procedure introduced herein for using the apparatus will be readily understood by present practitioners, who will require little or no additional training.

Other novel features which are characteristic of the invention, as to organization and method of operation, together with further objects and advantages thereof will be better understood from the following description considered in connection with the accompanying drawing in which a preferred embodiment of the invention is illustrated by way of example. It is to be expressly understood, however, that the drawing is for the purpose of illustration and description only and is not intended as a definition of the limits of the invention.

Certain terminology and derivations thereof may be used in the following description for convenience in reference only and will not be limiting. For example, such words as "upwardly," "downwardly," "leftwardly," and "rightwardly" will refer to directions in the drawings to which reference is made unless otherwise stated. Similarly, such words as "inwardly" and "outwardly" will refer to directions toward and away from, respectively, the geometric center of a device and designated parts thereof.

BRIEF DESCRIPTION OF THE DRAWING

FIG. 1 is a broken sectional perspective view showing perforation of the placental membranes by a physician with the electrode emplacement apparatus of this invention;

FIG. 2 is an enlarged broken sectional view of the apparatus and procedural step of FIG. 1; and FIGS. 3-5 are schematic views showing, in linear progression, the remainder of the electrode emplacement procedure, i.e. attachment of the scalp electrode and removal of the introducer sleeve apparatus.

DRAWING REFERENCE NUMERALS 1 electrode emplacement apparatus
4 introducer sleeve apparatus of 1
5 guide tube of 4
6 drive tube of 4
7 hook on 5
8 concave side of 4
10 convex side of 4
14 electrode
16 base of 14
18 wire from 14
22 finger
26 patient
28 vagina of 26
30 cervix of 26
32 membranes
34 hole in 32
40 fetus
42 scalp of 40
44 skull of 40

DESCRIPTION OF A PREFERRED EMBODIMENT

Referring to FIG. 1, there is illustrated therein the first step of the combined amniotomy and electrode emplacement procedure of this invention. The procedure is accomplished through the use of the electrode emplacement apparatus 1 introduced herein.

With further reference to the enlarged view of FIG. 2, it can be seen that the emplacement apparatus 1 includes a three-part introducer sleeve apparatus 4. Sleeve apparatus 4 comprises an outer hollow guide tube 5, a flexible drive tube 6 journaled within the guide tube, and a sharp pointed membrane perforator barb or hook 7. The hook is molded, or otherwise fixedly attached, on the side of the guide tube 5 near the forward end of the guide tube, and it projects radially outward therefrom. Barbless introducer sleeves are well-known in the art.

In addition to the introducer sleeve apparatus 4, the emplacement apparatus 1 includes an implantable helically coiled (spiral) pointed electrode 14, also of a form known in the art. The spiral electrode 14 is mounted within a cylindrical electrode base 16. Electrically conductive wires 18 connect to the electrode within the base 16 and lead out of the open rear end of the introducer sleeve apparatus 4 to a standard lock and grip stopper (not illustrated), from whence they are connectable to fetal heart rate monitoring apparatus. The introducer sleeve apparatus 4 provides means for introducing the electrode 14 into the birth canal of an expectant mother, as discussed below.

The forward end of the inner drive tube 6 abuts the piston-like electrode base 16, which base is also slideably journaled within the outer guide tube 5, near the open forward end thereof. The flexible inner drive tube 6 is free to push the base 16 and electrode 14 forward within the outer guide tube 5 and to twist the electrode about the common longitudinal axis of the tubes 5, 6, all in the manner known and described in the art.

The outer guide tube is generally cylindrical, but preferably is curved axially near its open forward end so as to have a concave side 8 and a convex side 10, as better seen in FIGS. 3-5. It is presently contemplated that the hook 7 will be most advantageously affixed to the concave side 8; however, it could alternatively be molded onto the convex side 10, or two hooks could be formed, one on each side. Furthermore, the invention would work with a straight introducer sleeve apparatus.

The barb or hook 7 may be shielded by the fingers 22 of the physician during the procedure, as shown in the drawing. Therefore, it is presently contemplated that a simple laterally projecting hook 7 will do, substantially as drawn. It is to be understood, however, that protection for tissue adjoining the membranes could be incorporated into the invention. For example, a ridge or similar raised area on the side of the guide tube 5 could precede the hook so as to guide tissue away from the hook, or the hook could be indented somewhat into the tube end, as is done, for example, in the AMNIHOOK brand membrane perforator. Furthermore, a mechanism might be added which would provide for extension and retraction of the hook before and after the amniotomy, perhaps one which is automatically activated by the adjustable position of the drive tube 6, or of the sliding base 16.

METHOD OF USE

The electrode emplacement apparatus 1 is used to perform a single combined amniotomy and fetal monitoring electrode emplacement procedure as follows.

First, the introducer sleeve apparatus 4 containing the electrode 14 and bearing the amniotomy hook 7 is introduced through the birth canal or vagina 28 of the pregnant patient 26 (FIGS. 1 and 2). The hook 7 is shielded or covered by the physician's fingers 22. The sleeve 4 is angled upward vertically so that its longitudinal axis generally approaches a tangential angle with the presenting part of the fetus 40, preferably the scalp 42 of its skull 44 (bony calvarium).

In this manner, the hook 7 may be brought to bear on the placental membranes 32, i.e. the amnion and the chorion, through the opening in the dilated or partially-dilated cervix 30. These thin membranes are under hydrostatic pressure and easily may be pierced with the sharp point of the hook. Next, (or simultaneously) by dragging the sleeve apparatus 4 and hook 7 tangentially upward (arrow A—upward with respect to true vertical), the membranes 32 will burst and a hole 34 will be opened. The membranes may then be retracted. Thus, the scalp 42 of the fetus 40 will be cleared for direct attachment of the electrode 14.

During the procedure thus far, the electrode is recessed within the guide tube 5, in order to protect it from being electrically fouled with detached pieces of the membranes 32 or the like. Because of this need to keep the coiled electrode 14 clean, it is not itself available to perform the amniotomy, though it is sharp enough to do so.

It should be noted that the size and shape of various organs, tissues and other parts are distorted in the drawing for purposes of illustration. For example, in FIGS. 1 and 3-5 the scalp 42, the membranes 32 and the hook 7 are all shown disproportionately larger than true scale. The optimal size of the hook 7 is yet to be determined; however, it is more likely to approach that shown in FIG. 2 than elsewhere in the drawing.

Turning to FIG. 3, after the amniotomy the apparatus 1 is *not* withdrawn from the vagina 28; rather, next the introducer sleeve 4 simply is re-oriented so as have its longitudinal axis X perpendicular (at its forward end) to the fetal scalp 42. The drive tube 6 is then used to push the electrode coil 14 out of the forward end of the guide tube 5 and into contact with the scalp 42.

The physician withdraws his or her hand and performs the traditional cork-screw maneuver (arrow B) with the introducer sleeve 4. Alternately, the physician may leave one hand in the vagina 28 (to hold the sleeve 4 perpendicular and the electrode 14 pressed against the scalp 42) while performing the cork-screw maneuver with the other free hand. This sinks the fetal scalp electrode 14 into the fetal scalp 42. It is to be noted that while the entire sleeve apparatus 4 may be turned, the electrode alternatively may be implanted by turning the drive tube 6 within the guide tube 5, also as is taught in the art.

Next, the physician releases the standard stopper (not illustrated) which clamps the wires 18 so as to temporarily hold the drive tube 6 and electrode base 16 abutted together in fixed relationship. If they have been removed in the previous step, then the physician's fingers 22 (preferably, the index and the middle fingers) are replaced on the forward end of the guide tube over or immediately adjacent to the hook 7, to prepare the introducing sleeve 4 for removal.

Lastly, the introducer sleeve 4 is removed from the patient's vagina 28 by withdrawing the guide and drive tubes up the wires 18. At this point, both tubes 5 and 6 travel together in the direction of arrow C, while the electrode 14 and the wires 18 remain stationary. The electrode remains embedded in the fetal scalp 42, where it is available to send signals reflecting the fetal heart rate up the wires 18 to appropriate monitoring and display equipment.

While the above provides a full and complete disclosure of the preferred embodiments of this invention, various modifications, alternate constructions, and equivalents may be employed without departing from the true spirit and scope of the invention. Such changes might involve alternate materials, components, structural arrangements, sizes, operational features or the like. Therefore, the above description and illustrations should not be construed as limiting the scope of the invention which is defined by the appended claims.

What is claimed is:

1. Electrode emplacement apparatus for amniotomy and fetal monitoring including:
   introducer sleeve means for introducing a monitoring electrode, the introducer sleeve means having a forward end;
   a monitoring electrode slideably recessed within the forward end; and
   hook means for rupturing amniotic membranes, the hook means fixedly attached to an outside surface of the forward end.

2. The apparatus of claim 1 wherein:
   the sleeve means is generally cylindrical and the hook means projects radially outward from a side of the forward end.

3. The apparatus of claim 2 wherein:
   the side of the forward end from which the hook means projects is curvedly concave with respect to a longitudinal axis of the sleeve means.

4. The apparatus of claim 2 wherein:
   the sleeve means has an outer hollow guide tube and the hook means is attached to the guide tube.

5. The apparatus of claim 4 further including:
   a drive tube journaled within the guide tube in abutment with the electrode.

6. The apparatus of claim 5 further including:
   wire means in electrical communication with the electrode and journaled within the drive tube.

7. Electrode emplacement apparatus for amniotomy and fetal monitoring including:
   a spiral fetal heart rate electrode having a first pointed end;
   an introducer sleeve comprised of an outer hollow guide tube having an open forward end and an inner hollow drive tube journaled within the guide tube in abutment with the electrode, the electrode recessed within the forward end;

conductive wire leading from the electrode and journaled within the drive tube; and a hook having a second pointed end, the hook projecting radially outward from a side of the guide tube near the forward end.

8. The apparatus of claim 7 wherein:

the side of the guide tube from which the hook projects is curvedly concave with respect to a longitudinal axis of the guide tube.

9. A method for performing an amniotomy and emplacing a fetal heart rate monitoring electrode including the steps of:

providing introducer sleeve means for introducing a monitoring electrode, the introducer sleeve means having a forward end, a monitoring electrode slideably recessed within the forward end, and hook means for rupturing amniotic membranes, the hook means fixedly attached to an outside surface of the forward end;

introducing the sleeve means into a vagina of a patient having amniotic membranes and bearing a fetus;

rupturing the amniotic membranes with the hook means; and without first removing the hook means from the vagina, attaching the electrode to the fetus of the patient.

10. The method of claim 9 further including the steps of:

after attaching the electrode, removing the sleeve means from the vagina; and shielding the hook means with fingers of a physician both when the sleeve means is introduced into the vagina and when it is removed therefrom.

11. The method of claim 9 wherein:

the electrode is attached by maneuvering the sleeve means in a cork-screw manner.

12. The method of claim 9 wherein:

the sleeve means has a longitudinal axis at the forward end and the longitudinal axis is at a generally tangential angle to a scalp of the fetus when rupturing the amniotic membranes with the hook means, and is at a generally perpendicular angle to the scalp when attaching the electrode to the fetus.

13. A method for performing an amniotomy and emplacing a fetal heart rate electrode including the steps of:

providing a spiral fetal heart rate electrode having a first pointed end;

providing an introducer sleeve comprised of an outer hollow guide tube having an open forward end and an inner hollow drive tube journaled within the guide tube in abutment with the electrode, the electrode recessed within the forward end;

providing conductive wire leading from the electrode and journaled within the drive tube;

providing a hook having a second pointed end, the hook projecting radially outward from a side of the guide tube near the forward end;

introducing the sleeve into a vagina of a human patient having amniotic membranes and bearing a fetus;

rupturing the amniotic membranes with the hook; and without first removing the hook from the vagina, attaching the spiral electrode to the fetus of the patient.

14. The method of claim 13 further including the steps of:

after attaching the spiral electrode, removing the sleeve from the vagina; and shielding the hook with fingers of a physician when the sleeve is introduced and removed from the vagina.

15. The method of claim 14 wherein:

the spiral electrode is attached by maneuvering the sleeve in a cork-screw manner.

16. The method of claim 15 wherein:

the sleeve has a longitudinal axis at the forward end and the longitudinal axis is at a generally tangential angle to a scalp of the fetus when rupturing the amniotic membranes with the hook, and is at a generally perpendicular angle to the scalp when attaching the spiral electrode to the fetus.

* * * * *